United States Patent [19]
Reinhard et al.

[11] Patent Number: 5,911,994
[45] Date of Patent: Jun. 15, 1999

[54] **EXTRACT FROM *SALVIA OFFICINALIS* FOR USE IN THE TREATMENT OF DUPUYTRENS'S CONTRACTURE**

[75] Inventors: Max Reinhard, Bad Homburg; Walter Wolpert, Friedrichsdorf, both of Germany

[73] Assignee: Heilmittelbetrieb Isernhagen GmbH, Bad Homburg, Germany

[21] Appl. No.: 09/063,776

[22] Filed: Apr. 22, 1998

[30] Foreign Application Priority Data

Apr. 29, 1997 [EP] European Pat. Off. .............. 97107064

[51] Int. Cl.⁶ .................................................... A61K 35/78
[52] U.S. Cl. ........................................................... 424/195.1
[58] Field of Search ............................................ 424/195.1

[56] References Cited

U.S. PATENT DOCUMENTS

| 4,942,033 | 7/1990 | Aubert et al. | 424/195.1 |
| 5,660,831 | 8/1997 | Reinhard | 424/175.1 |

FOREIGN PATENT DOCUMENTS

| 0 147 331 | 7/1985 | European Pat. Off. . |
| 0 454 097 A1 | 10/1991 | European Pat. Off. . |
| WO 88/02260 | 4/1988 | WIPO . |

*Primary Examiner*—Herbert J. Lilling
*Attorney, Agent, or Firm*—Griffin, Butler, Whisenhunt & Szipl, LLP

[57] ABSTRACT

The use of an extract from *Salvia officinalis* for producing a medicament for combating Dupuytren's contracture is described, the extract coming in particular from the flowers thereof.

4 Claims, No Drawings

EXTRACT FROM *SALVIA OFFICINALIS* FOR USE IN THE TREATMENT OF DUPUYTRENS'S CONTRACTURE

FIELD OF THE INVENTION

The invention relates to the use of an extract from *Salvia officinalis* (sage) for producing a medicament for combating Dupuytren's contracture.

BACKGROUND OF THE INVENTION

Dupuytren's contracture arises from unknown causes and is a progressive, scarry shrinkage and thickening of the flexion contracture of the cusp-like extended palmar aponeurosis in the palm of the hand, whereby, as the curvature of the fingers increases, especially that of the fourth and fifth fingers, stretching of the fingers becomes ever more restricted. This ailment, which attacks men more frequently than women and can occur in one or both hands, begins with a dimple-like indentation in the palm of the hand and gradually but quite painlessly grows into nodules and fascicles. The flexor tendons of the fingers concerned are not in themselves diseased but their movement is impaired by the scar-fascicles of the palmar aponeurosis. A similar contracture concerning the toes is known.

Since the illness neither regresses spontaneously nor responds with any degree of long term success to conventional forms of treatment (without surgery) such as massage, heat treatment and the like, it can only be treated surgically, namely, by cutting away the proliferating atrophied tissue. Apart from the unpleasantness associated with any surgical operation, it has transpired that the scars resulting from the operation can make a later recurrence of the ailment even worse.

SUMMARY OF THE INVENTION

The object of the invention is to provide a medicament for treating Dupuytren's contracture.

Surprisingly, it has been discovered that an extract suitable for combating Dupuytren's contracture can be produced from sage (*Salvia officinalis*). In consequence, the subject of the invention is the use of an extract from *Salvia officinalis* (sage) for producing a medicament for combating Dupuytren's contracture.

The preferred extract for treating this illness is an extract from the flowers of *Salvia officinalis*.

The use of aqueous solutions of constituents from the leaves of the sage plant to counteract excessive perspiration, catarrhs and as medications for flushing and gargling is already known. Such solutions are obtained for example by treating the sage leaves with hot water. Apart from the actual extraction step, utilising e.g. alcohol, the conventional methods of obtaining sage extracts have included a step involving distilling off the extraction vehicle at temperatures of over a 100° C. Many constituents are thereby changed or thermally damaged.

Furthermore, the use of extracts from flowers of sage for treating high blood pressure, circulatory disorders and disorders arising in the healing of wounds is known from WO 94/906217 (=U.S. Pat. No. 5,660,831).

DESCRIPTION OF PREFERRED EMBODIMENTS

The extraction from *Salvia officinalis* can be effected with the aid of any extracting means such as water, organic solvents or supercritical $CO_2$. One example of an organic solvent is ethanol. As already mentioned, the temperature during extraction, and in any subsequent stage required for at least partial removal of the extractant such as by distillation for example, should be 50° C. or less and preferably 40° C. or less so as to prevent thermal impairment of the constituents of the sage plant. In the case of distillative separation, this means that the pressure must be reduced to the extent necessary for maintaining the stated upper temperature limit.

The use of supercritical $CO_2$ for the sage extraction process is particularly preferred as it can be carried out at low temperatures and is thus a particularly gentle process.

Extraction using supercritical $CO_2$ may be effected in any apparatus suitable therefor. The lower limits for the temperature and pressure during the extraction process arise from the thermodynamic properties of $CO_2$, namely, a critical temperature of 31.3° C. and a critical pressure of 71.5 bar.

In particular, it is preferred to work at a temperature of 40° C. or below when extracting with $CO_2$. The pressure should preferably lie in the range from 90 to 300 bar.

Extraction may be continued until all of the constituents extractable from *Salvia officinalis* by using supercritical $CO_2$ have been extracted therefrom. This is usually the case for this extraction process after a period of 1 to 2 hours. However, it is possible to extract just a portion of the constituents of *Salvia officinalis*.

One advantage of using supercritical $CO_2$ as the extractant as compared to the use of other extractants such as ethanol or water, is that extraction can be effected at temperatures below 40° C., whereas a conventional extraction process using alcohol for example requires the ethanol to be distilled off at temperatures of more than 100° C.

A further advantage of extracting with supercritical $CO_2$ is that solventless extracts can be obtained. This thus avoids the healing power of the extract from being unduly affected by solvents such as ethanol.

The extract used in accordance with the invention is preferably obtained from flowers of *Salvia officinalis*. After harvesting, the flowers are preferably dried i.e. at a temperature of 40° C. or below. Just as for the extraction temperature, a comparatively low drying temperature is chosen so as to permit the flowers of sage to be treated in a gentle manner. It is also feasible to utilise deep frozen flowers.

The extract from the flowers of *Salvia officinalis* has a paste-like consistency. This extract may be used as the effective constituent of the medicament. The medicament is preferably provided in the form of an injectable preparation. A liquid carrier agent is not required as the sage extract being used is itself liquid at temperatures of 30 to 40° C. A local anaesthetic is preferably added to the preparation so that the surrounding area is simultaneously numbed when the preparation is injected. Any conventional local anaesthetic may be used, in a ratio of 1:1 with the extract.

For the purposes of treatment, the injectable preparation is injected directly into that area of the affected tendon at which the main tension occurred. Due to this injection, inflammation occurs in the curtailed area of the tendon. The oedema associated therewith renders the tendon tissue capable of extension in a natural manner. Elongation of the tendon can be achieved in this phase by constant nagging (i.e. gently and continuously urging or nudging), thus resulting in an improvement in the functioning of the finger. The treatment is preferably repeated several times at intervals of one or more weeks.

The invention will be explained in more detail hereinafter by means of examples.

EXAMPLE 1

This example concerns the production of a $CO_2$-induced, total extract from flowers of *Salvia officinalis*. For this purpose, hand-picked, dried flowers were extracted for 2 hours at a pressure of 300 bar (total extraction) and a temperature of 40° C. using $CO_2$. 623 g of extract were obtained thereby from 15.2 kg of sage flowers. This corresponds to an extract yield of 4.1%. The extract obtained was in the form of a paste.

EXAMPLE 2

This example is concerned with obtaining a $CO_2$-induced, selective extract from flowers of *Salvia officinalis*. The extraction conditions comprised an extraction period of 2 hours, a pressure of 90 bar (selective extraction) and a temperature of 40° C. 14 g of extract were obtained thereby from the 1.7 kg of dried flowers being used. This corresponds to an extract yield of 0.8%. The extract obtained was in the form of a paste.

EXAMPLE 3

Example of Treatment

A male patient (60 years of age) who suffered from Dupuytren's contracture of the fourth and fifth fingers of the left hand received an injection of the preparation in accordance with Example 2 (at a dosage of 0.2 ml per finger) in the area of the affected tendons. An oedema was formed as a result of the injection. Elongation of the tendon could be achieved by constant nagging. This treatment was carried out 3 times altogether (with pauses of several weeks between each treatment).

The following improvement was achieved:
Initial condition:
 Bent contraction of the ring finger: 30°
 of the little finger: 90°
After three series of injections each of 0.2 ml of the preparation, the following values were obtained after a total period of four weeks:
 ring finger active: 5°
 little finger active: 30°
 ring finger passive: 0°
 little finger passive: 10°
 "active" means: The finger can be raised up without using force.
 "passive" means: The finger can be bent back as far as possible using force (using the other hand for example).

While flowers of *Salvia officinalis* are preferred other parts of the plant, such as the roots, the leaves or the stalks or combinations thereof may be made use of for the extraction.

The extraction process may occur in analogous manner to that described for the extraction from flowers. Further while the invention was discribed hereinbefor with reference to the Dupuytren's contracture of the fingers (aponeurosis palmaris) a similar contracture of the toes (aponeurosis plantaris) may be treated by means of the present invention.

What is claimed is:

1. A method for the treatment of Dupuytren's contracture which comprises administering to a patient suffering from Dupuytren's contracture an effective amount of an extract prepared by immersing a portion of a *Salvia officinalis* plant in an extraction medium selected from the group consisting of water, organic solvents, and supercritical carbon dioxide, maintaining said *Salvia officinalis* in said extraction medium at a temperature of 50° C. or less for a period sufficient to allow said extract to be extracted by said extraction medium, and recovering said extract from said extraction medium.

2. The method of claim 1, wherein said extract is an extract from flowers of *Salvia officinalis*.

3. The method of claim 1, which comprises injecting said extract directly into that area of an affected tendon at which a main tension occurred.

4. A method for the treatment of Dupuytren's contracture which comprises administering to a patient suffering from Dupuytren's contracture an effective amount of an extract prepared by immersing *Salvia officinalis* flowers in an extraction medium comprising carbon dioxide, maintaining said *Salvia officinalis* flowers in said extraction medium at a temperature of about 40° C. and a pressure of about 90 bar for a period of about two hours, and recovering said extract from said extraction medium.

* * * * *